United States Patent [19]

Lohrmann

[11] Patent Number: 5,014,717
[45] Date of Patent: May 14, 1991

[54] PUNCH-BIOPSY APPARATUS WITH CANNULA-AIMING DEVICE

[76] Inventor: Günter Lohrmann, Hagenstrasse 20, 2060 Bad Oldesloe, Fed. Rep. of Germany

[21] Appl. No.: 479,106

[22] Filed: Feb. 12, 1990

[30] Foreign Application Priority Data

Feb. 10, 1989 [DE] Fed. Rep. of Germany ....... 3903956

[51] Int. Cl.$^5$ .............................................. A61R 10/00
[52] U.S. Cl. .................................................. 128/754
[58] Field of Search ................ 128/749, 751, 753, 754

[56] References Cited

U.S. PATENT DOCUMENTS

| | | | |
|---|---|---|---|
| 3,595,217 | 7/1971 | Rheinfrank | 128/754 |
| 3,732,858 | 5/1973 | Banko | 128/753 |
| 4,010,737 | 3/1977 | Vilaghy et al. | 128/754 |
| 4,142,517 | 3/1979 | Starropoulos et al. | 128/754 |
| 4,266,555 | 5/1981 | Jonshidi | 128/754 |
| 4,314,565 | 2/1982 | Lee | 128/753 |
| 4,600,014 | 7/1986 | Beraha | 128/754 |
| 4,681,123 | 7/1987 | Valtcher | 128/754 |

FOREIGN PATENT DOCUMENTS 0921526 4/1982 U.S.S.R. ............................ 128/754

Primary Examiner—Max Hindenburg
Attorney, Agent, or Firm—Herbert Dubno

[57] ABSTRACT

A punch biopsy apparatus with a cannula-aiming device has a trocar braced against the end of the punch at one extremity and formed with a finger guide for the finger of the surgeon at the opposite end. To adjust the effective length of the trocar and thereby precisely control the depth of penetration, the first extremity of the trocar is provided with a tapered guide allowing insertion of the cannula and the stylet passing therethrough. The guide is externally threaded and is surrounded by an internally threaded adjustment sleeve rotatable relative to the guide. At the other end of the adjustment sleeve a clamping nut secures the adjustment sleeve against the trocar tube once the effective length has been set.

10 Claims, 2 Drawing Sheets

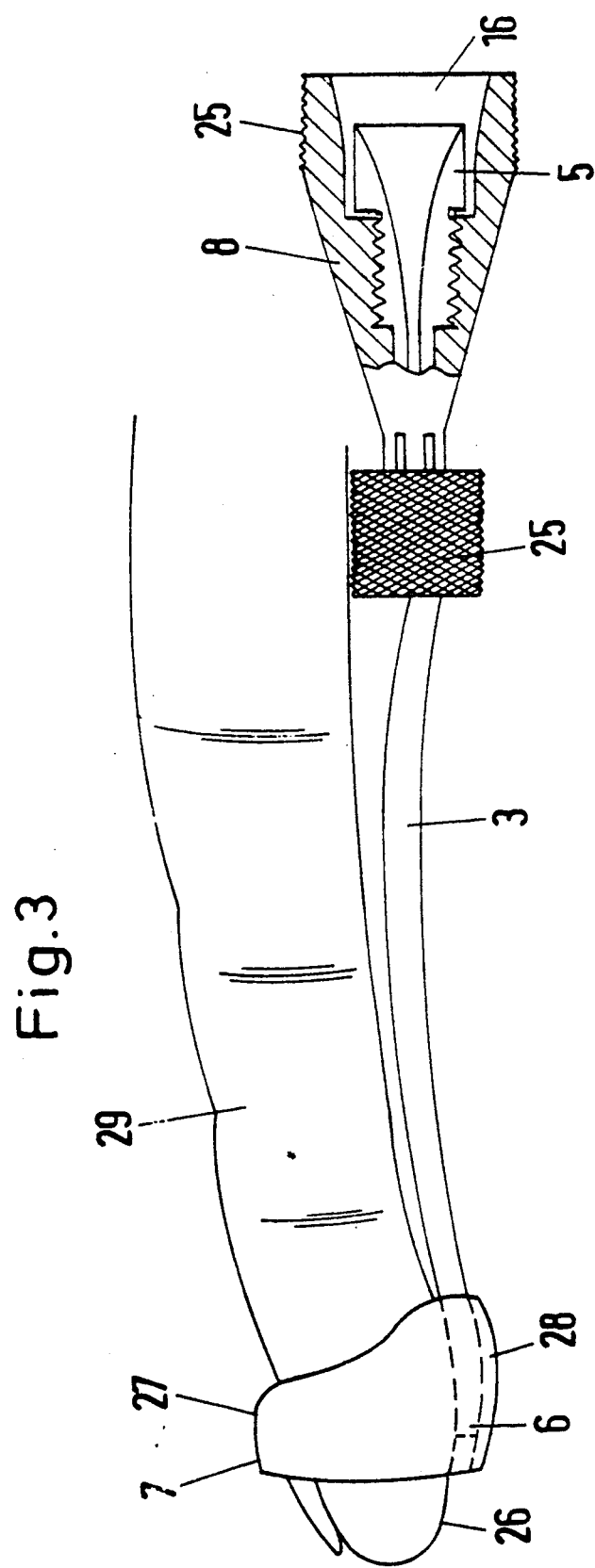

PUNCH-BIOPSY APPARATUS WITH CANNULA-AIMING DEVICE

FIELD OF THE INVENTION

My present invention relates to a punch-biopsy apparatus with a cannula-guiding and aiming device and, more particularly, to an aiming device for a punch-biopsy cannula combined with a biopsy punch, for the examination of the human prostate by biopsy.

BACKGROUND OF THE INVENTION

An important means for the early diagnosis of carcinoma of the prostate is a rectal examination. Hard areas and palpable nodules are recommended for an examination by biopsy. Carcinoma cells are found to be present in about 50% of all cases with suspect nodules. In these cases, tissue samples obtained by so-called punch biopsy have proved to be particularly useful.

Most urologists long ago discarded the earlier method of obtaining a transrectal punch biopsy by means of a punch-biopsy cannula with an outside diameter of more than 2 mm. The reason was the high incidence of complications due to injury and bleeding in the region of the rectal mucosa, because the cannula's outside diameter was too great and direct digital guidance (in a sterile glove) was essential for penetrating to the region of the intestinal mucosa, prostate, and capsule. Without an aiming device for the punch cannula, the procedure was relatively painful and time-consuming, and could be performed only on in-patients and under general anesthesia.

For outpatient treatment in the urologist's consulting rooms, the only feasible method was the transperineal access for punch biopsy. If outpatient treatment was considered at all, then the preferred method for this was under local anesthesia. However, the great majority of prostate punch biopsies is still performed on in-patients under local or general anesthesia.

The position changed to some extent with the introduction of an instrument for punch biopsy, the so-called biopsy system. This system consists of a punch which houses the complete mechanical system for controlling the procedure for taking a cylindrical tissue sample from the prostate by a punch-biopsy cannula comprising a sleeve-shaped knife and a stylet which slides within the knife. The punch has a spring-loaded control which times the action of the stylet and sleeve-shaped knife to ensure that they shoot out suddenly and in the proper sequence into the tissue, and that the punch and the cutting mechanism work properly.

To obtain a tissue sample, the surgeon guides the cannula from the perineum toward the capsule of the prostate and releases the punch. The time interval between the movement of the mandrin and of the knife is only a few hundredths of a second. When the cannula is released, it shoots out about 23 mm. After the puncture, the cover of the punch can be opened, the biopsy cannula taken out, the stylet moved forward, and the tissue sample in the recess of the stylet removed. The punch can then be cocked again for the next puncture. Reference may be had to U.S. Pat. No. 4,600,014 and BIOPSY-CUT AN AUTOMATIC SYSTEM FOR BIOPSY ..., Nier Blase Prostata, March 1988, Pages 15–17.

Since the system described above has become commercially available, it has been used increasingly for punch biopsies on outpatients in the urologist's consulting rooms, because it permits a fast punching procedure and provides greater precision for obtaining tissue material of consistently good quality for pathological examination.

Force of habit among urologists and the lack of a suitable aiming system for the punch-biopsy cannula has resulted in continued use of the transperineal access. But this suffers from the disadvantage that, to reach the prostate, the biopsy cannula has to travel relatively far in passing through the perineum, and one can never be certain of striking any specific areas of the prostate with suspicious changes.

A further major disadvantage of this system is the fact that the puncture cannula advances about 23 mm during the biopsy process. This distance is fixed and cannot be adjusted. In patients with a very small prostate, after hormone therapy, or after resection, this puncture depth may be greatly excessive. In such cases, the probe may penetrate beyond the organ and, for example, puncture the bladder, the urethra or a periprostatic venous plexus.

OBJECTS OF THE INVENTION

It is an object of the present invention, therefore, to provide an aiming device for the purposes described which permits the performance of a transrectal punch biopsy free from risk, under the surgeon's direct palpatory control.

Another object of the invention is to provide a prostate biopsy apparatus which is simple to operate, accurate to position and safe.

SUMMARY OF THE INVENTION

The invention overcomes this difficulty by a trocar which accommodates and surrounds the cannula. One end of the trocar is proximal to the punch. The other projects beyond the tip of the biopsy cannula when the punch is cocked.

More particularly, the biopsy apparatus can comprise:
- an elongated biopsy punch adapted to be cocked and triggerable for prostate biopsy;
- a variable length trocar having one extremity positionable adjacent an end of the punch and an opposite extremity engageable with a finger of a medical practitioner for alignment with a prostate region from which a biopsy is to be taken, the variable-length trocar having
  an elongated tube terminating at the other end,
  a guide funnel engaging the elongated tube at the one extremity, formed with an external thread, and braced against the end of the punch,
  an adjustment sleeve having an internal thread threadedly engaging the external thread at on end of the sleeve and rotatable relative to the guide funnel to adjust an effective length of the trocar, the adjustment sleeve being formed at an opposite end thereof with an external screw thread, and
  means engageable with the external thread at the other end of the adjustment sleeve for clamping the adjustment sleeve against the tube; and
- a biopsy cannula having a cutting edge recessed inwardly of the opposite extremity in a cocked position of the punch and projecting from the opposite extremity by a predetermined penetration distance adjusted by adjustment of the effective length upon triggering of the punch, the biopsy cannula passing through the trocar into the punch and being displaceable thereby relative to the trocar.

The aiming device permits pain-free examination. The examination itself is much faster, is suitable or use on outpatients, and no longer calls for the use of local anesthetics. It therefore avoids possible side-effects, such as cardiovascular disturbances and allergic reactions. It makes recourse to the longer transperineal access to the prostate unnecessary, much of which has had to be traversed 'blind'. A biopsy can now be performed directly on the organ, under the surgeon's direct, sensitive, palpatory digital control, at greatly reduced risk of injury to healthy regions. The device allows the use of the anatomically most suitable and most logical access for obtaining tissue material from the prostate.

The length adjustability of the aiming device allows adjustment of the depth of puncture from 8 mm to 20 mm. It permits proper biopsies of even abnormally small prostates and of the suspect tumor areas which are generally located near the capsule.

Further, it permits multiple biopsies without the need for additional anesthetics. Biopsies are also possible on very old, sensitive, high-risk patients. The anatomically correct shape of the aiming device, the very thin punch-biopsy cannula, and the short-like speed of the puncturing process all reduce to extremely rare cases the risk of complications due to injury and bleeding.

BRIEF DESCRIPTION OF THE DRAWING

The above and other objects, features and advantages of my invention will become more readily apparent from the following description, reference being made to the accompanying highly diagrammatic drawing in which:

FIG. 3 is a side view of an aiming device in accordance with FIG. 2, with a finger of the examining surgeon inserted in the finger guide.

SPECIFIC DESCRIPTION

Figure 1:
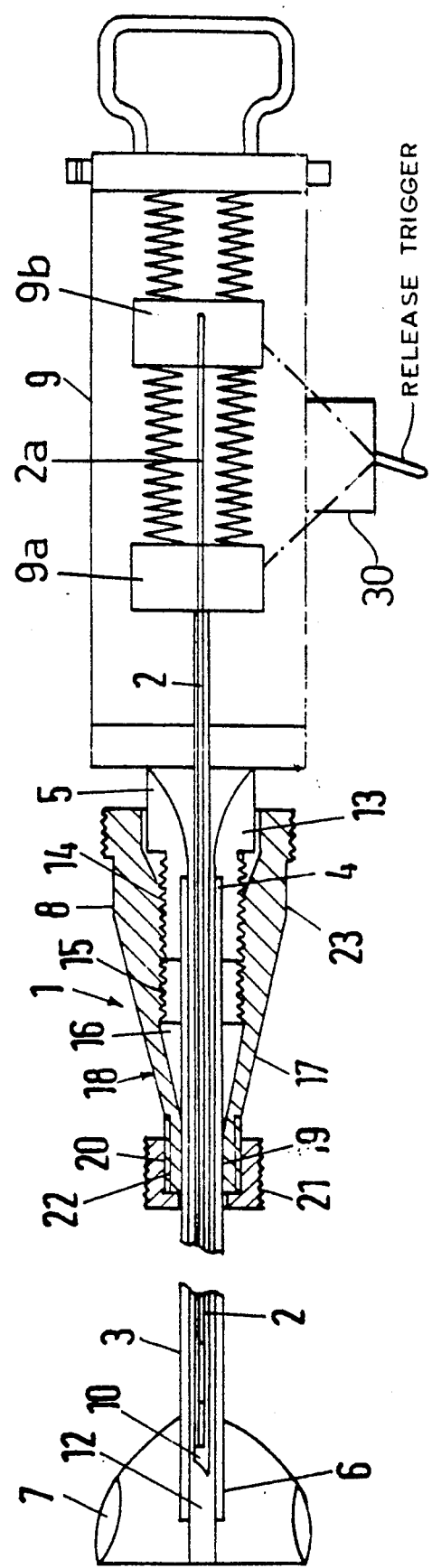
FIG. 1 is a diagrammatic view from above of a punch with an attached aiming device in section, wherein the aiming device is shown adjusted to its minimum length.
Figure 2:
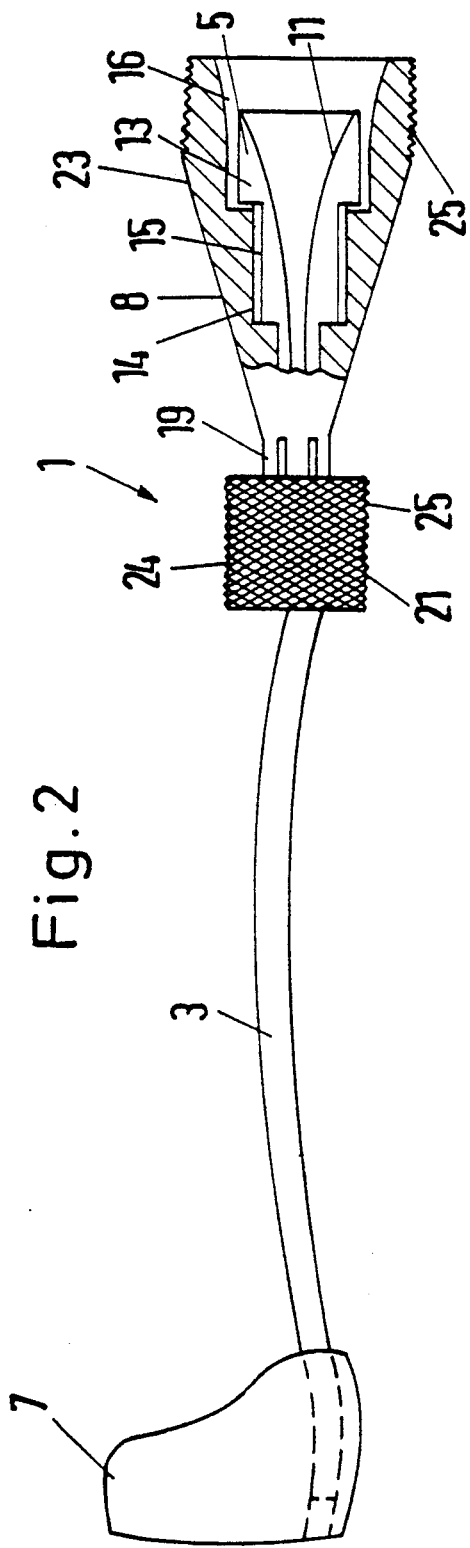
FIG. 2 is a partial side view of an aiming device in accordance with FIG. 1, wherein the aiming device is shown adjusted to its maximum length.

The main components of the aiming device 1 are a trocar 3 which accommodates and surrounds a punch biopsy cannula 2. One end 4 of the trocar 3 has a guide funnel 5 and the other end 6 has a finger guide 7 and an adjustment sleeve 8 which radially surround the trocar 3 and the guide funnel 5.

In the preferred embodiment, the trocar 3 has an outside diameter of 3 mm and an inside diameter of 2 mm, and accommodates the punch-biopsy cannula 2. When the punch-biopsy cannula 2 is inserted in a biopsy punch 9 and the cannula 2 is placed in the trocar 3, the cannula 2 is hidden so completely in the trocar 3 that the other end of the trocar 3 just covers the tip 10 of the cannula 2 when the punch 9 is cocked ready for taking a tissue sample.

The end 4 proximal to the punch 9 is firmly secured to the guide funnel 5, whose inside diameter 11 tapers toward the trocar 3. There is a smooth (flush) transition from the guide funnel 5 to the inside 12 of the trocar 3. The outside walls of the guide funnel 5 are essentially cylindrical in shape. The guide funnel 5 has an external thread 14 which fits in the internal thread 15 of an adjustment sleeve 8 that radially surrounds the guide funnel 5. The internal thread 15 of the adjustment sleeve 8 can be turned about the outside thread 14 by rotation of the externally knurled sleeve 8 to produce a longitudinal displacement. The adjustment sleeve 8 contains an inner space 16 in which the trocar 3 with the guide funnel is so arranged that it can slide lengthwise to permit the longitudinal adjustment of the aiming device 1.

On the outside 17, the adjustment sleeve 8 tapers distally of the punch 9. Distally of the punch 9, the adjustment sleeve 8 has a clamping piece 19 consisting of a tapered thread 20 over which fits the internal thread 22 of a tapered clamping sleeve nut 21.

When the clamping sleeve nut 21 is screwed tightly on the thread 20 of the clamping piece 19, the clamping piece 19 receives the trocar 3 and clamps it in position like the engagement of a rod by a collet or chuck.

The adjustment sleeve 8 and the sleeve nut 21 have outer surfaces 23 and 24 finished with cross-knurling 25 to provide a better grip.

At its end 6 distally to the punch 9, the trocar 3 has a finger guide 7 shaped to fit the examining surgeon's fingertip 26. The finger guide 7 is formed as a sleeve 27 rounded off in all directions, through whose wall 28 the trocar 3 passes at least partly in a direction which is substantially parallel with that of the surgeon's finger. The finger guide 7 is firmly attached to the trocar 3. The trocar 3 is shaped to fit the surgeon's finger 29 and palm.

As described in connection with the BIOPSY-CUT system, the cannula tube which is displaced by one spring loaded member 9a of the punch 9 can be traversed by a stylet 2a actuated by a second spring loaded member 9b of the punch.

The aiming device 1 is used as follows:

After palpation of the patient's prostate and determining the location of suspicious changes, the urologist decides on the area of the prostate from which a tissue sample is to be taken and particularly the depth to which the biopsy cannula 2 is to penetrate when the punch 9a released.

When this has been done, the cannula 2 is laid in the uncocked punch 9 and the tip 10 of the cannula 2 is introduced through the guide funnel 5 into the trocar 3 until the tip 10 projects out of the trocar 3 at the other end 6 near the finger guide 7. In accordance with the depth previously determined to which the cannula 2 is to penetrate into the patient's prostate, the clamping sleeve nut 21 is slackened on the thread 20 of the clamping piece 19 to free the adjustment sleeve 8 with its internal thread 15 to move over the outside thread 14 of the guide funnel 5. By rotation of the adjustment sleeve 8 relative to the guide funnel 5, the overall length of the aiming device 1 is freely adjustable until the cannula 2 projecting from the end 6 of the trocar 3 has the required depth of penetration. The clamping sleeve nut 21 is again screwed tightly on the thread 20 of the clamping piece 19 to ensure that the aiming device 1 is of the required overall length. After withdrawal of the cannula together with the punch 9 from the trocar 3 and the guide funnel 5, the punch 9 is cocked and the cannula 2 is reintroduced into the trocar 3 via the guide funnel 5. With the punch 9 cocked, the tip 10 of the cannula 2 lies hidden inside 12 of the trocar 3.

The biopsy instrument with the aiming device 1 is now prepared for taking a tissue sample.

The examining surgeon introduces the tip 26 of his index finger in the finger guide 7 and supports the aiming device 1 and the adjacent area of the punch 9 on his palm.

The surgeon places his fingertip 26 in the rectum of the patient to be examined, in such a way that it lies over the area of the prostate that is to be investigated. He can now guide the end 6 of the trocar 3 under direct palpatory control to the biopsy site and release the punch 9 by actuating its trigger 30.

When the punch 9 is released, the sample is taken from the prostate in a fraction of a second. The punch 9 with the cannula 2 is removed from the aiming device 1 and the tissue sample obtained is removed from the cannula. During this, the aiming device 1 with the surgeon's finger 29 can remain in its original position.

When the tissue sample has been removed from the cannula 2 and the punch 9 is cocked again, for example by an assistant, the procedure can be repeated several times. This keeps the strain on the patient exceptionally low. In particular, the risks attendant on the multiple administration of a local anesthetic and the inconvenience of in-patient treatment are obviated. In particular, the biopsy cannula 2 does not have to pass through the perineum repeatedly. Moreover, the length adjustment of the aiming device 1 which this device permits reliably removes the risk of a prostate-puncture error and of injury to other organs.

I claim:

1. A punch-biopsy apparatus for prostate biopsy, comprising:
   - an elongated biopsy punch adapted to be cocked and triggerable for prostate biopsy;
   - a variable length trocar having a first extremity positionable adjacent an end of said punch and a second extremity opposite said first extremity engageable with a finger of a medical practitioner for alignment with a prostate region from which a biopsy is to be taken, said variable-length trocar having
   - a guide funnel formed with an external thread and braced against said end of said punch,
   - an adjustment sleeve surrounding said guide funnel, said adjustment sleeve having an internal thread threadedly engaging said external thread at a first end of said sleeve and rotatable relative to said guide funnel to adjust an effective length of said trocar, said adjustment sleeve being formed with an external screw thread at a second end thereof opposite said first end,
   - an elongated tube connecting said guide funnel to said second extremity, and
   - means engageable with said external thread at said second end of said adjustment sleeve for clamping said adjustment sleeve against said tube; and
   - a biopsy cannula having a cutting edge recessed inwardly of said second extremity in a cocked position of said punch and projecting from said second extremity by a predetermined penetration distance adjusted by adjustment of said effective length upon triggering of said punch, said biopsy cannula passing through said trocar into said punch and being displaceable thereby relative to said trocar.

2. The punch-biopsy apparatus for prostate biopsy defined in claim 1 wherein said guide funnel has an internal funnel-shaped surface merging smoothly into an inner wall of said tube and is firmly attached thereto.

3. The punch-biopsy apparatus for prostate biopsy defined in claim 2 wherein said guide funnel has substantially cylindrical outer walls.

4. The punch-biopsy apparatus for prostate biopsy defined in claim 2 wherein said adjustment sleeve tapers conically away from said punch.

5. The punch-biopsy apparatus for prostate biopsy defined in claim 4 wherein said means engageable with said external thread at said second end of said adjustment sleeve for clamping said adjustment sleeve against said tube includes an externally knurled nut threaded onto said external thread at said second end of said adjustment sleeve.

6. The punch-biopsy apparatus for prostate biopsy defined in claim 5 wherein said adjustment sleeve is externally knurled at said first end of said adjustment sleeve to facilitate rotation thereof.

7. The punch-biopsy apparatus for prostate biopsy defined in claim 2 wherein said second extremity of said trocar is formed with a finger guide shaped to receive a fingertip of said medical practitioner.

8. The punch-biopsy apparatus for prostate biopsy defined in claim 7 wherein said finger guide is formed as a sleeve rounded off in all directions and having a wall through which said tube passes at least partially parallel to the finger of the medical practitioner.

9. The punch-biopsy apparatus for prostate biopsy defined in claim 8 wherein said finger guide is affixed to said tube.

10. The punch-biopsy apparatus for prostate biopsy defined in claim 9 wherein said trocar is shaped to fit said finger and a palm of the medical practitioner.

* * * * *